United States Patent [19]

Marsoner et al.

[11] Patent Number: 5,130,009
[45] Date of Patent: Jul. 14, 1992

[54] SENSOR DEVICE

[75] Inventors: Hermann Marsoner, Steinberg; Helmut List, Graz; Heinz Kontschieder, Graz; Falko Skrabal, Graz, all of Austria

[73] Assignee: AVL Medical Instruments AG, Schaffhausen, Switzerland

[21] Appl. No.: 469,214

[22] Filed: Jan. 24, 1990

[30] Foreign Application Priority Data

Jan. 27, 1989 [AT] Austria .................. A170/89

[51] Int. Cl.[5] .................. G01N 27/31; G01N 27/327
[52] U.S. Cl. .................. 204/403; 204/153.12; 204/153.17; 204/409; 204/412; 204/415; 204/435; 435/817; 436/806
[58] Field of Search .................. 204/403, 415, 416–420, 204/435, 153.12, 153.17, 412, 409; 435/817; 436/806

[56] References Cited

U.S. PATENT DOCUMENTS

| 3,151,052 | 9/1964 | Arthur et al. | 204/409 |
| 3,770,607 | 11/1973 | Williams | 204/415 |
| 4,073,713 | 2/1978 | Newman | 204/403 |
| 4,324,256 | 4/1982 | Vesterager | 204/415 |
| 4,356,074 | 10/1982 | Johnson | 204/403 |
| 4,452,682 | 6/1984 | Takata et al. | 204/403 |
| 4,891,104 | 1/1990 | Liston et al. | 204/415 |

FOREIGN PATENT DOCUMENTS

0048090A3 8/1981 .

*Primary Examiner*—T. Tung
*Attorney, Agent, or Firm*—Watson, Cole, Grindle & Watson

[57] ABSTRACT

In order to produce a small-volume flow measuring cell with good flow characteristics in a sensor device for determining the concentration of a substrate in a sample medium, comprising an enzyme electrode which is covered by a membrane and a reference electrode, both of which are in contact with the measuring cell, the proposal is put forward that the reference electrode be located outside of the membrane cover of the enzyme electrode and that the maximum extension of the flow measuring cell normal to the flow direction of the sample medium essentially be the same as the diameter of the sensitive layer of the enzyme electrode.

9 Claims, 1 Drawing Sheet

SENSOR DEVICE

BACKGROUND OF THE INVENTION

This invention relates to a sensor device for determining the concentration of a substrate in a sample medium, comprising a membrane-covered amperometric enzyme electrode and a reference electrode, both of which are in contact with a flow measuring cell.

In many applications of medicine or biotechnology the accurate determination of a particular substrate concentration in a sample medium, e.g., the concentration of glucose in a perfusion solution, is of prime importance. For such purposes electrochemical sensors are used frequently, whose basic measuring principle will be explained below, using the determination of $\beta$-D-glucose as an example.

According to common practice amperometric methods using a constant polarisation voltage Up are particularly well suited for substrate determination. In such methods $\beta$-D-glucose is converted within a membrane containing the enzyme glucose oxidase (GOD) in immobilized form, according to the reaction equation given below;

$\beta$-D-glucose + $O_2$ $\xrightarrow{GOD}$ gluconic acid + $H_2O_2$

The hydrogen peroxide formed during this process may be detected via anodic oxidation at a platinum electrode:

$H_2O_2 \rightarrow O_2 + 2H^+ + 2e^-$

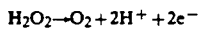

$Up = 600 \ldots 700 \, mV$

The intensity of the sensor current depends on the concentration of glucose in the sample solution.

Amperometric determination of glucose with the use of enzyme sensors is practicable only if both certain chemical and geometrical requirements are fulfilled. For example, the surface of the anode must be large enough to ensure sufficient sensitivity of the sensor. A large surface also is required for the reference electrode, by means of which the electric circuit is closed. A large, non-polarizable reference electrode will permit unimpeded collection of the sensor current.

DESCRIPTION OF THE PRIOR ART

A sensor device as described at the beginning of this paper is discussed in EP-A 0 048 090, for instance. It is provided with a flow measuring cell, one side of which is formed by an electro-chemical thin-film cell. This cell consists of an enzyme layer situated between an inner and an outer membrane, the inner membrane being pressed against a support holding platinum anode and an Ag/AgCl-reference electrode in concentric arrangement. The thin-film cell is fastened to the support by means of an O-ring. The outer membrane of this cell is in contact with the sample introduced into the measuring cell, and within a short time oxygen and the substrate to be determined will enter into the thin-film cell by diffusion and react with the enzyme of the enzyme layer. In the course of this process hydrogen peroxide is produced, which will diffuse through the inner membrane and initiate the corresponding test reaction at the platinum anode.

Other electrode arrangements are known where the appropriate enzyme is directly immobilized on the platinum anode, the actual enzyme electrode being surrounded by an annular reference electrode and the entire electrode device being covered by a rubber membrane.

The disadvantage of the known devices is that they usually have a complicated design and comparatively large sample chambers with poor flow characteristics, whose dimensions are directly related to the diameter of the electrode arrangement.

SUMMARY OF THE INVENTION

It is an object of this invention to improve a sensor device of the type as described at the beginning of this paper, in such a way that a small-volume flow measuring cell with good flow properties may be built, which will retain the measuring sensitivity of the original design, and that the entire device may be produced in a most simple manner.

In the invention this object is achieved by positioning the reference electrode outside of the membrane cover of the enzyme electrode and by providing that the maximum extension of the flow measuring cell normal to the flow direction of the sample medium essentially be the same as the diameter of the sensitive layer of the enzyme electrode. It has been found unexpectedly that membrane-free reference electrodes, which may be placed either in front of or behind the actual enzyme electrode in flow-direction of the sample medium, will give excellent test results while permitting most compact measuring cells with good flow characteristics, whose width normal to the direction of flow is essentially determined by the diameter of the actual enzyme electrode. The good flow characteristics will prevent sample components from forming deposits in the measuring cell and thus facilitate cleaning.

In a preferred variant of the invention which will permit further reduction of the volume of the measuring cell, the flow measuring cell has two opposite faces, one containing the sensitive layer of the enzyme electrode and the other one of the membrane-free reference electrode, preferably an Ag-electrode. Another advantage of externally situated membrane-free reference electrodes is that in sensor devices with replaceable electrodes it is only the actual enzyme electrode that has to be replaced, whereas the separate reference electrode, which is more or less maintenance-free, may remain in the device.

In many measuring situations a further parameters of the sample liquid must be determined in addition to substrate concentration, for example, its conductivity or impedance. In order to keep the design of the device as compact as possible, it is proposed in this context that the reference electrode be devised as part of an electrode arrangement for impedance measurement, the corresponding complementary electrode preferably being located in the surface of the flow measuring cell opposite of the reference electrode. Whereas the enzyme electrode as well as the reference electrode should have comparatively large surfaces, the complementary electrode need not be more than a thin metal pin, preferably a silver wire, dipping into the flow measuring cell. In order to save space it should be positioned in front of the enzyme and reference electrodes facing each other, as seen in the direction of flow.

A sensor device in which conductivity and impedance are measured in addition to the concentration of the substrate, is mainly employed in the measuring of perfusion solutions that have been brought into contact with the tissue of an organism, where only partial equilibration is achieved between the perfusion solution and the test substrate in the tissue. The extent of equilibration is determined by the changing conductivity of the perfusion solution, and the actual concentration of the substrate may be calculated even if there is only partial equilibration.

According to a further development of the invention the complementary electrode of the electrode arrangement for impedance measurement is formed by the anode of the enzyme electrode. This will make possible two different measuring methods, i.e. either the enzyme concentration and impedance are determined in alternating order, or an alternating voltage for impedance measurement is superimposed on the polarization voltage for enzyme measurement, the two signals being separated and evaluated electronically.

In the context of impedance measurements and also in view of the temperature-dependent reactions in the enzyme sensor it is important to obtain information on the temperature of the sample medium. According to another variant of the invention, which is particularly simple to produce, a temperature sensor, preferably an NTC resistor, is inserted into a bore in the housing of the flow measuring cell, which bore is coaxial with and opposite of the complementary electrode. In this way a most compact flow cell is obtained for continuous determination of the substrate concentration, impedance and temperature of a sample medium.

Finally, the invention provides that the enzyme electrode be configured as a glucose sensor. The glucose oxidase enzyme may be immobilized directly on the platinum anode or in a carrier membrane in a conventional manner.

DESCRIPTION OF THE DRAWING

Following is a more detailed description of the invention as illustrated by the attached drawing, in which.

DETAILED DESCRIPTION OF PREFERRED EMBODIMENTS

Figure 1:
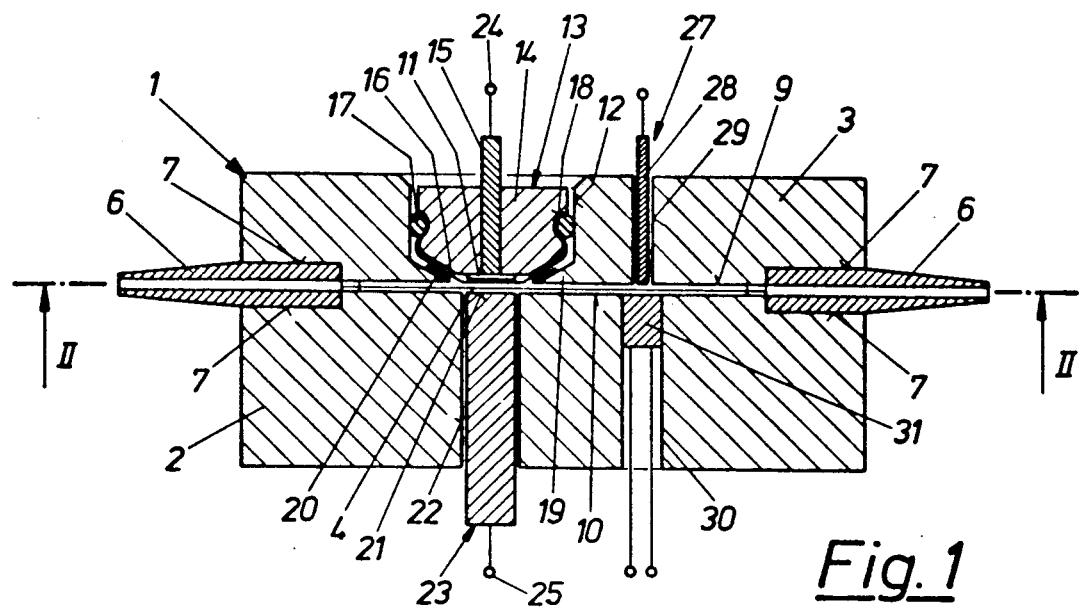
FIG. 1 presents a section of a sensor device according to the invention, along line I—I in FIG. 2.
Figure 2:
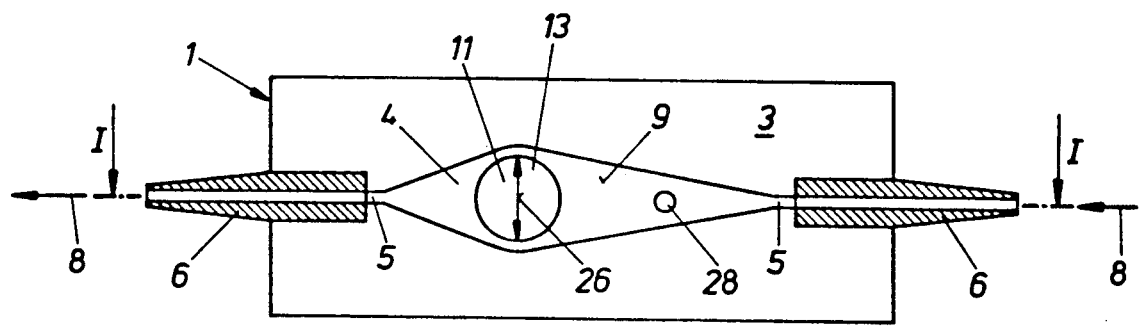
FIG. 2 presents a section along line II—II in FIG. 1.

The sensor device shown in FIG. 1 has a two-part housing 1, whose lower part 2 and upper part 3 are glued together in the plane of the measuring chamber configured as a flow measuring cell 4. As is seen in FIG. 2, the measuring cell 4 has capillary bores 5 both at its inlet and outlet end, which bores 5 are provided with fittings 6 that are held in recesses 7 of the lower part 2 and upper part 3 and are sealed in place when the two parts of the housing are glued together. The flow direction of the sample medium is indicated by arrows 8.

The flow measuring cell 4 is bounded by two opposing faces 9 and 10, one of which, i.e., 9, contains the sensitive layer 11 of the enzyme electrode 13 located in an opening 12 of the upper part 3.

The enzyme electrode 13 has a supporting part 14 in whose center a platinum anode 15 has been inserted. On the side of the measuring cell the end of the platinum anode 15 is in contact with the sensitive layer 11 or an enzyme membrane, which in turn is covered by an outer membrane 16. The membrane 16 is held by an O-ring 17 sitting in an annular groove 18 of the supporting part 14. The O-ring 17 will also ensure that the enzyme electrode 13 is held in place in the opening 12 of the housing 1 by frictional forces. On the side of the measuring cell 1 a sealing element 20 is provided, which presses against a projecting rim 19 of the opening 12, sealing the enzyme electrode against the upper part 3 of the housing.

The surface 10 of the flow measuring cell 4 opposite of the enzyme electrode 13 holds the front end 21 of the reference electrode 23 located in a bore 22 of the lower part 2. The electric leads of the enzyme electrode 13 and the reference electrode 23 have the reference numbers 24 and 25.

Due to the external position of the reference electrode 23 the volume of the measuring cell 4 is kept small and good flow characteristics are achieved, and the maximum extension of the measuring cell 4 normal to the flow direction of the sample medium is essentially the same as the diameter 28 of the sensitive layer 11 of the enzyme electrode 13.

Both parts of the measuring cell may be injection-moulded from an electrically insulating material, such as plexiglass, the various bores or openings required for the individual electrodes could also be made with drilling or cutting tools, however.

The degree of equilibration of perfusion solutions may be determined by measuring the electric impedance between two metal electrodes in contact with the perfusion solution. As the reference electrode 23 is accessible from outside it may be used as part of an electrode arrangement 27 for impedance measurement. The corresponding complementary electrode 28, which is located in a bore 29 of the upper part 3, ends at the surface 9 of the measuring cell 4 opposite of the reference electrode 23.

It is also possible to use the anode 15 of the enzyme electrode 13 as a complementary electrode 28 for impedance measurement, which will further simplify the device.

Finally, a temperature sensor 31 is located in a bore 30 in the housing 1 of the flow measuring cell 4, which bore is coaxial with and situated opposite of the complementary electrode 28. For this purpose a polished NTC resistor is used preferably. The miniaturized flow measuring cell is thus suitable for simultaneous determination of the substrate concentration, degree of equilibration and temperature of a sample. The volume of the measuring cell need not exceed 15 microliters, for instance.

Figure 3:
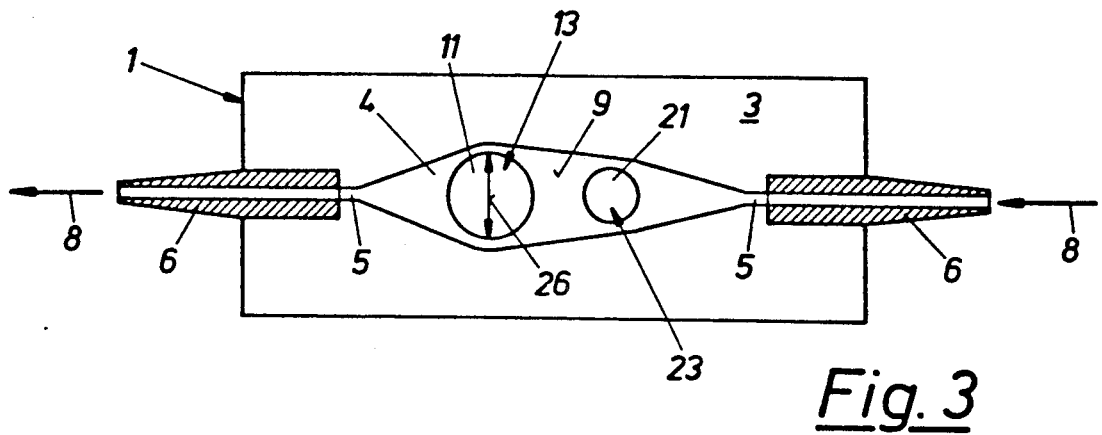
FIG. 3 presents a section as in FIG. 2 of another variant of the invention.

FIG. 3 shows another variant of the invention, in which both the enzyme electrode 13 and the membrane-free reference electrode 23 are located in one and the same face of the measuring cell 4. Again, a measuring cell with good flow properties is obtained, whose maximum width essentially is the same as the diameter 26 of the sensitive layer 11 of the enzyme electrode 13.

We claim:

1. A sensor device for determining the concentration of a substrate in a sample medium, said device comprising a plurality of electrodes and a membrane, only one of said plurality of electrodes being covered by said membrane, said one electrode being an amperometric, enzyme anode, and another of said plurality of electrodes being a reference electrode positioned outside the membrane cover of said enzyme anode, both said anode and reference electrodes being in contact with a flow measuring cell, said cell being a hollow channel located in a housing which comprises two housing parts, said channel defined by opposite faces of the two housing parts, wherein the maximum extension of said flow measuring cell normal to the flow direction of said sample medium is essentially the same as the diameter of a sensitive layer of said amperometric enzyme anode, and wherein one of said faces contains said sensitive layer of said amperometric enzyme anode and the other of said faces contains said reference electrode.

2. A sensor device according to claim 1, wherein said reference electrode is an Ag-electrode.

3. A sensor device according to claim 1, wherein said reference electrode also constitutes a part of an electrode arrangement for impedance measurement and a further electrode of said plurality of electrodes being a corresponding complementary electrode of said electrode arrangement, said further electrode being located in said face containing said sensitive layer of said amperometric enzyme anode and being positioned outside the membrane cover.

4. A sensor device according to claim 3, wherein said complementary electrode of said electrode arrangement for impedance measurement is formed by said anode of said amperometric enzyme electrode.

5. A sensor device according to claim 4, wherein said amperometric enzyme anode is configured as a glucose sensor.

6. A sensor device according to claim 3, wherein a temperature sensor is inserted into a bore of said housing of said flow measuring cell, said bore being coaxial with and opposite of said complementary electrode.

7. A sensor device according to claim 6, wherein said temperature sensor is an NTC resistor.

8. A sensor device according to claim 1, wherein said amperometric enzyme anode is configured as a glucose sensor.

9. A sensor device according to claim 6, wherein said amperometric enzyme anode is configured as a glucose sensor.

* * * * *